(12) United States Patent
Persson et al.

(10) Patent No.: US 9,332,922 B2
(45) Date of Patent: May 10, 2016

(54) SOLUTION FOR INTERNAL MONITORING OF BODY

(75) Inventors: Mikael Persson, Alingsas (SE);
Andreas Fhager, Gothenburg (SE);
Parham Hashemzdaeh, Gothenburg (SE)

(73) Assignee: MEDFIELDS DIAGNOSTICS AB, Gothenburg (SE)

( * ) Notice: Subject to any disclaimer, the term of this patent is extended or adjusted under 35 U.S.C. 154(b) by 901 days.

(21) Appl. No.: 12/306,823

(22) PCT Filed: Jun. 29, 2007
(Under 37 CFR 1.47)

(86) PCT No.: PCT/SE2007/000647
§ 371 (c)(1),
(2), (4) Date: Sep. 2, 2009

(87) PCT Pub. No.: WO2008/002251
PCT Pub. Date: Jan. 3, 2008

(65) Prior Publication Data
US 2010/0174179 A1    Jul. 8, 2010

Related U.S. Application Data

(60) Provisional application No. 60/806,105, filed on Jun. 29, 2006.

(51) Int. Cl.
*A61B 6/00* (2006.01)
*A61B 5/05* (2006.01)
*A61F 2/46* (2006.01)
(Continued)

(52) U.S. Cl.
CPC ............. *A61B 5/05* (2013.01); *A61B 5/0507* (2013.01); *A61B 5/4076* (2013.01); *A61F 2/4657* (2013.01); *A61B 5/4528* (2013.01); *A61B 5/7207* (2013.01); *A61F 2/32* (2013.01); *A61F 2002/3067* (2013.01); *A61F 2002/4658* (2013.01); *A61F 2002/48* (2013.01); *A61F 2250/0002* (2013.01)

(58) Field of Classification Search
None
See application file for complete search history.

(56) References Cited

U.S. PATENT DOCUMENTS 3,721,900 A * 3/1973 Andrews .................... 324/95
5,829,437 A * 11/1998 Bridges .................... 600/430
(Continued)

FOREIGN PATENT DOCUMENTS

EP 0694282 1/1996
WO 99/33399 7/1999
(Continued)

OTHER PUBLICATIONS

EP Search Report dated Oct. 14, 2009 from corresponding EP Application 07748306.
(Continued)

*Primary Examiner* — Long V Le
*Assistant Examiner* — Bradley Impink
(74) *Attorney, Agent, or Firm* — Young & Thompson

(57) ABSTRACT

A device, method, and system for monitoring the status of an internal part of a body using an electromagnetic transceiver operating in the microwave regime; a processing unit compares measured data with reference data to determine the status of the internal part. The solution may be arranged to continuously monitor the internal part of the body and the system may be arranged so as to be wearable or portable.

17 Claims, 6 Drawing Sheets

(51) Int. Cl.
    *A61B 5/00*    (2006.01)
    *A61F 2/32*    (2006.01)
    *A61F 2/30*    (2006.01)
    *A61F 2/48*    (2006.01)

(56) References Cited

U.S. PATENT DOCUMENTS

| | | | |
|---|---|---|---|
| 6,064,903 | A | 5/2000 | Riechers et al. |
| 6,233,479 | B1 | 5/2001 | Haddad et al. |
| D454,670 | S | 3/2002 | Weller |
| 6,454,711 | B1 | 9/2002 | Haddad et al. |
| 7,122,012 | B2 | 10/2006 | Bouton et al. |
| 7,226,415 | B2 | 6/2007 | Haddad et al. |
| 2003/0018244 | A1 | 1/2003 | Haddad et al. |
| 2003/0036674 | A1 | 2/2003 | Bouton |
| 2003/0036713 | A1 | 2/2003 | Bouton et al. |
| 2003/0088180 | A1 | 5/2003 | Van Veen et al. |
| 2004/0249258 | A1 | 12/2004 | Tupin et al. |

FOREIGN PATENT DOCUMENTS

| | | |
|---|---|---|
| WO | 00/15109 | 3/2000 |
| WO | 00/64343 | 11/2000 |
| WO | 03/009753 | 2/2003 |
| WO | 2006028397 | 3/2006 |

OTHER PUBLICATIONS

International Search Report dated Oct. 16, 2007, from corresponding PCT application.
European Office Action, dated Nov. 5, 2013, from corresponding EP application.

* cited by examiner

SOLUTION FOR INTERNAL MONITORING OF BODY

TECHNICAL FIELD

The present invention relates to a solution for detecting status of internal parts of the body, e.g. the brain and in particular to a solution using electromagnetic radiation in the microwave region for intermediate or continuous monitoring.

BACKGROUND OF THE INVENTION

Non-invasive techniques for diagnosis and determination of status of humans or animals are increasingly winning ground since these pose low risk for the patient and are usually low cost as compared to invasive techniques. Especially considering the brain, non-invasive techniques may provide convenient and safe ways of determination of the brain status. However, the common techniques for this are not able to determine all types of parameters of need, which means that there are blind spots where invasive techniques are still used.

Furthermore, some non-invasive techniques provide solutions where the patient is still put in risk of danger, for instance where x-rays are used the patient will be subjected to a dose of radiation potentially harmful and it can in many cases not be used for continuously or semi-continuously (i.e. intermittently) monitor the status of parameters in the brain (or in any other part of the body).

Some of the known non-invasive techniques will give some information but there is a need for getting more information about the monitored part.

Medical instrumentation is quite expensive due to their complex nature and can often only be used for one type of ailment.

One application of the invention deals with the task of detecting increased intracranial pressure (ICP) by means of electromagnetic radiation in the microwave region. The standard method to monitor brain swelling resulting from head injury is by measuring the intracranial pressure. A pressure probe is inserted through a burr hole in the skull bone and the mean pressure is registered on an hourly basis. If the pressure raises several treatments is activated where the most extreme one is surgical removal of parts of the skull bone (craniectomy) to allow brain swelling to occur without the dangerous pressure increase. If incidents of severe brain swelling could be better predicted the treatment could be more selective and provide an overall better result in the treatment. At present monitoring of the semi-static intracranial pressure (ICP) is the main basis for the treatment of brain swelling of different etiologies. As done today, ICP is measured at one point intracranially. The probe cannot detect pressure gradients and cannot say anything about the cause of a possible increase of the ICP. There can be development of substantial contusions and even hematomas of potentially life-threatening magnitude, before the measured ICP increases significantly. A special case when this risk is high is when there is a need for continuous deviation of cerebrospinal fluid. Today, the monitored data cannot give enough information to reliably predict all episodes of dangerously high ICP. This is a common clinical experience. Hence, there is a clinical need for new sensor systems.

With today's technique of making a hole in the skull to insert a pressure probe is a significant risk associated that the patient will develop an infection in the vicinity of the hole. The largest benefit with the present invention is that it can be made completely non-invasive and thus all the risks associated with ICP measurements today can be eliminated.

Another area of application for the current invention is in diagnosing stroke patients by means of a sensor system that can be used in an ambulance for assessments of patient with suspected stroke. Internationally ambulance service paramedics have been trained to use a stroke recognition tool to speed up transfer and assessment of patients with suspected stroke. This facilitates the time critical intervention of thrombolysis which has been shown to improve the outcome from ischaemic stroke if given in time. The proposed system develops this one step further by providing additional information to be able to distinguish between ischaemic and haemorrhagic stroke.

Microwave techniques can provide non-invasive, easy access, to the human brain at a relatively low cost providing a large amount of multi frequency scattering data that can be used to analyze the continues developments of the dielectric and geometric properties of the human brain. Developments of the methods in the project may result in an imaging modality for traumatic brain injury patients allowing for a continuous bedside brain imaging system. It would also be possible to extend the method to include monitoring of other parts of the body, e.g. the abdomen in case of suspected internal bleeding. In that case the antenna system has to be suitably designed but the analysis could be done with the same equipment as for the brain monitoring.

SUMMARY OF THE INVENTION

It is an object of the present invention to provide a solution that remedies at least some of these problems. This is provided for in a number of aspects in which a first is a device for obtaining a representation of the status of internal parts of a body part, comprising
    a processing unit;
    an interface to a microwave transceiver;
    a display unit;
    wherein the processing unit is arranged to:
        repeatedly send a control signal to the microwave transceiver for generating a pulse of microwave radiation to be radiated from at least one antenna into the body part;
        receive signals indicative of received microwave radiation from the microwave transceiver;
        analyze the received signals with respect to time and amplitude; compare the analyzed signals with theoretically or measured reference data;
        determine the status of the internal part of the body from the comparison.

The device may be arranged to analyze the signals with reference to a brain, a hip joint, the stomach, or some other internal part of the body.

The device may be arranged to analyze the signals with reference to an initial measurements of the internal part of the body.

The device may be arranged to continuously monitor the status of the internal part of the body.

The device may be arranged to analyze the data in real time.

The processing unit may be arranged to use information relating to polarization, amplitude, and phase in analysis.

The processing unit may be arranged to eliminate data relating to body movement. The processing unit may be arranged to base the elimination on an inverse Fourier transform of measured data into the time domain and use the first reflection as an indication of movement.

Another aspect of the present invention, a method for obtaining a representation of the status of internal parts of a body is provided, comprising the steps of
repeatedly sending a control signal from a processing unit to a microwave transceiver;
receiving signal indicative of received microwave signals from the microwave transceiver;
analysing the received signals with respect to time and amplitude;
comparing the analyzed signals with theoretically or measured reference data;
determining the status of the internal parts of the body using the comparison in a continuous manner.

Yet another aspect of the present invention, a system for obtaining a representation of the status of internal parts of a body is provided, comprising:
a processing unit;
a microwave generating unit;
a microwave receiving unit;
at least one microwave transmitting antenna;
at least one microwave receiving antenna;
wherein the processing unit is arranged to control the microwave generating unit to generate a pulse of microwave radiation transmitted using the antenna, arranged to obtain signals from the microwave receiving unit in turn using the antenna for receiving signals reflected from internal parts of the body, and arranged to analyse the obtained signals with respect to time and amplitude, compare the result with reference data, and obtain a representation of the internal parts of the body.

The system may further comprise a transmitting antenna and a separate receiving antenna or a combined transmitting and receiving antenna.

The system may comprise a plurality of antennas arranged in a pattern at least partly surrounding the body part.

The transmitting antenna may be arranged to transmit circularly polarized radiation and the receiving antenna is arranged to receive at least elliptically polarized radiation.

The processing unit may be arranged to use information relating to polarization, amplitude, and phase in analysis.

The processing unit may be arranged to continuously monitor the status of a brain.

The processing unit may be arranged to detect volumetric or pressure changes relating to the brain.

The processing unit may be arranged to monitor an internal part of the body on a continuous time basis.

The processing unit may be arranged to determine a position vector from a plurality of s-vectors:

$$X=(s_{11}(\omega_1), s_{12}(\omega_1), \ldots, s_{nn}(\omega_1), s_{11}(\omega_2), \ldots, s_{nn}(\omega_m))$$

for a system comprising n number of antennas and m number of frequencies.

The system may be arranged to be portable or wearable.

The present invention provides a number of advantages as compared to known techniques for instance the solution is non-invasive, it may be used on several types of ailments (with the same equipment) leading to a more efficient use of instrumentation using the solution according to the present invention, furthermore, additional information about the ailment or status of the body may be collected. Also, since the radiation is in microwave regime with low interactive levels the solution may be used for continuous measurements without harming the patient.

BRIEF DESCRIPTION OF THE DRAWINGS

In the following the invention will be described in a non-limiting way and in more detail with reference to exemplary embodiments illustrated in the enclosed drawings, in which.

DETAILED DESCRIPTION OF PREFERRED EMBODIMENTS

Figure 1:
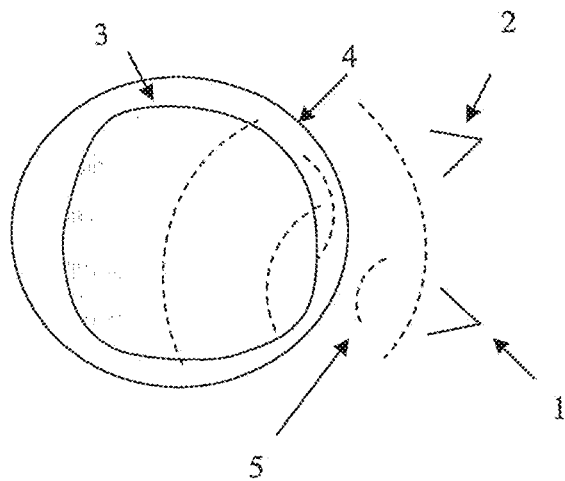
FIG. 1 illustrates schematically monitoring setup according to the present invention, in this case utilizing one transmitter and one receiver. The skull is illuminated with electromagnetic radiation that is scattered and detected by the receiver.
Figure 2:
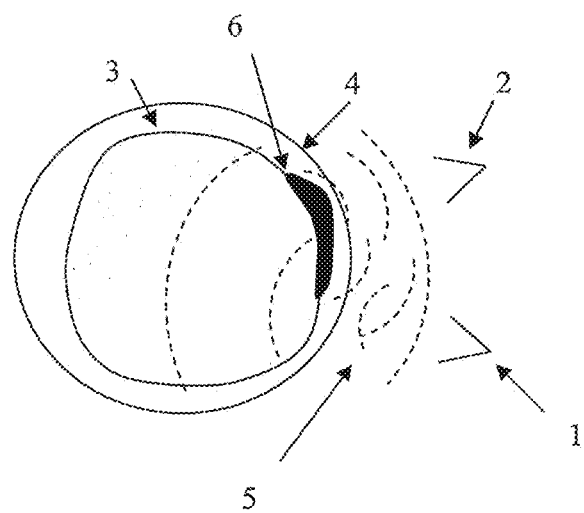
FIG. 2 illustrates schematically the monitoring setup of FIG. 1, with a volume increase inside the skull.

In FIG. 1, reference numeral 1 generally indicates a microwave transmitting device (an antenna) and 2 a microwave receiving device. In this example of application of the present invention, these are used to transmit electromagnetic radiation in the microwave regime into a body part (e.g. a head of a human). In this case the body part comprise an outer shell structure 4 (a skull) and an internal structure 3 (a brain). The microwave radiation is depicted with dashed lines 5. In FIG. 2 a deviation 6 form the normal internal structure is present (e.g. a tumor or a part with a different internal pressure due to aggregation of fluid (e.g. water or blood). This deviation 6 will cause the reflected waves to behave differently than for a structure without such deviation.

In FIG. 2, the skull is illuminated with electromagnetic radiation that is scattered and detected by the receiver 2. This figure shows a situation from FIG. 1 with a volume increase inside the skull, the black part 6 representing the location of the swelling 6 of the brain 3. The scattered radiation 5 is altered and picked up by the receiver 2.

Microwave techniques can provide non-invasive, easy access, to the human brain at a relatively low cost. This is accomplished by illuminating the skull with electromagnetic radiation that is propagating through and scattered from the different tissues inside the skull. The scattered radiation is carrying the information utilized by this invention for the purpose of detecting and analyzing a possible volume change of the tissue inside the skull and to relate this to an increased ICP (increased intracranial pressure). It will also constitute a method to distinguish between ischemic and hemorrhagic stroke. The system constituting the current invention collects a large amount of frequency components in the measurement that is analyzed to extract the necessary information. In this case frequencies in the range from about 100 MHz to about 5 GHz or more can be utilized. The system proposed here may be used to monitor traumatic brain injury patients for example by a continuously monitoring bedside system. It would also be possible to extend the method to include monitoring of other parts of the body, e.g. the abdomen in case of suspected internal bleeding. It could also be used as a system, for example in an ambulance, for diagnosis of stroke patients. The radiation exerted during the monitoring is of a non damaging type and level and may therefore be used for continuous monitoring of internal parts of the body.

This system is detecting changes in the brain e.g. caused by brain swelling or bleeding by observing the nature of the scattered radiation. The measurements are represented as a multi dimensional vector comprising S-matrix elements at a single frequency or alternatively a large number of frequencies. In a measurement with n number of antennas and m number of frequencies, $\omega_1$-$\omega_m$, the position vector could be expressed as $$X=(s_{11}(\omega_1),s_{12}(\omega_1), \ldots ,s_{nn}(\omega_1),s_{11}(\omega_2), \ldots ,s_{nn}(\omega_m)). \quad (1)$$

Changes in this vector indicate changes inside the skull and are related to the above mentioned injuries or diseases.

Figure 3:
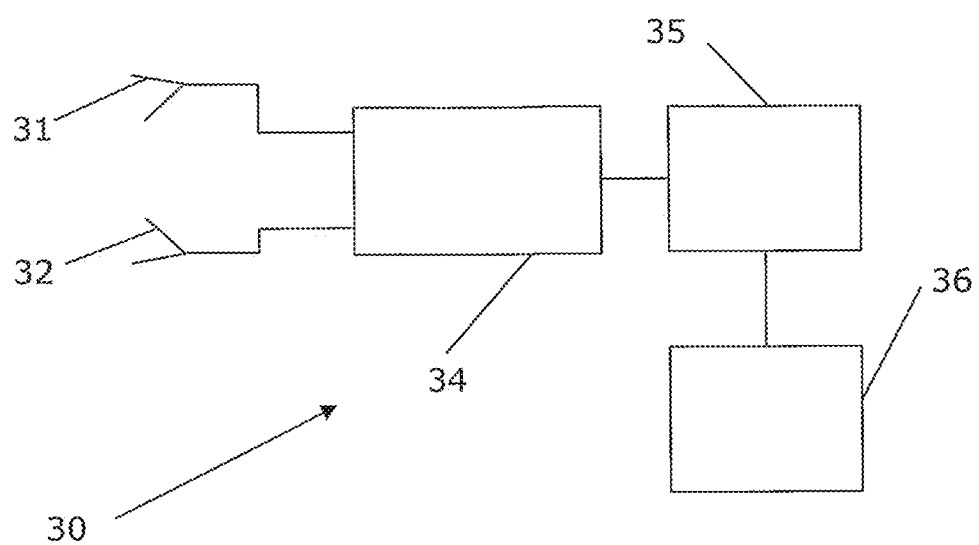
FIG. 3 illustrates schematically a system according to the present invention of a brain monitoring equipment.
Figure 9:
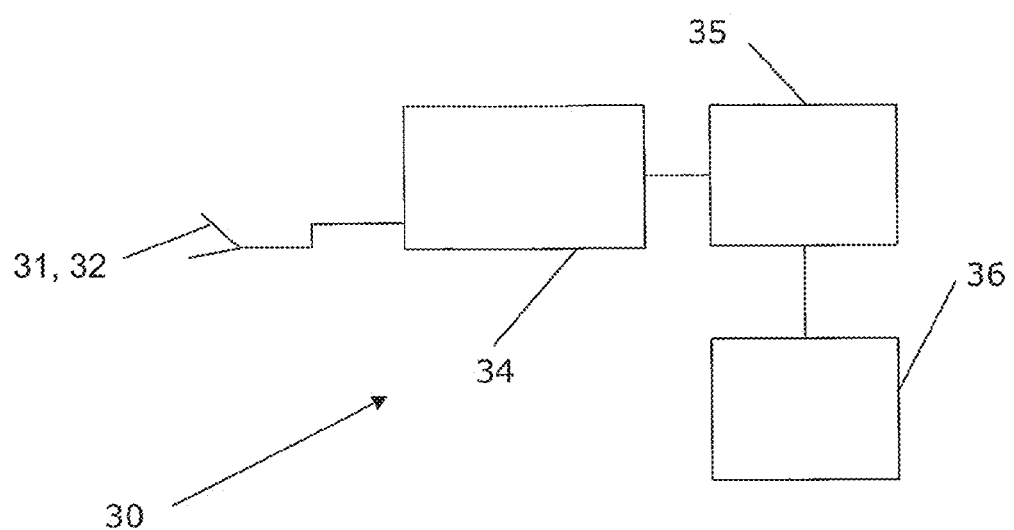
FIG. 9 illustrates schematically another system of the present invention.

The monitoring system comprises a transmitter of electromagnetic waves that is placed outside the skull and transmits electromagnetic radiation towards the head. Some portion of the radiation is scattered directly of the skin and some portion is penetrating inside the skull and scattered off the different internal tissues. One or more receivers outside the head are detecting the scattered radiation which is later processed 5 by a monitoring algorithm to detect the pressure increase. A schematic sketch of the antenna configuration can be seen in FIG. 1. FIG. 1 shows one transmitter irradiating the skull and one receiver picking up the scattered radiation. This is only an example of a system configuration. Another configuration of the system may comprise at least one antenna 10 acting both as transmitter and receiver. It could also comprise at least one separate transmitter and at least one separate receiver positioned around the skull. In the case of a volume increase the scattered radiation will be affected and the corresponding change in the measured scattered radiation will change. This change in the field can be detected and related to a change of the ICP. FIG. 2 shows the process of volume increase in the 15 brain that is detected by the present invention from its effect on the scattered radiation. The antennas transmitting and receiving the microwaves are driven by a signal generator and connected to a receiving unit. After the measurement the analysis of the data is made by the data analysis unit and the result is displayed on a screen, see FIG. 3. In FIG. 3 the data analysis unit 35 is used for controlling the measurement and analyses the data. The 20 data analysis unit is arranged to send a signal to a signal generator, e.g. a microwave transceiver 34 which in turn transmits microwave radiation to a transmitting antenna 31 and receives reflected radiation in a receiving antenna 32. It should be noted that these two antennas may be combined in one antenna (FIG. 9) and in such case advantageously a switching mechanism (not shown) is arranged in the path between the antenna and the microwave 25 transceiver inside the transceiver or as an external device. The switching mechanism may be used in order to not transmit directly into a receiving unit in the transceiver possibly saturating the input electronics. The transceiver may comprise two more or less separate units, a transmitting unit and a receiving unit, or it may be built into one single unit with electronics for each function built into the single unit. The data analysis unit 35 is further 30 arranged to control the display unit 36 to show the analysed data. Data analysis may be performed at another location by sending (through a network connection or using storage devices) measurement data to an analysis device, e.g. a central server or central computational device for post analysis and/or for storing of 35 measurement data in a central storage facility.

Data analysis may be performed at another location by sending (through a network connection or using storage devices) measurement data to an analysis device, e.g. a central server or central computational device for post analysis and/or for storing of measurement data in a central storage facility.

Figure 8:
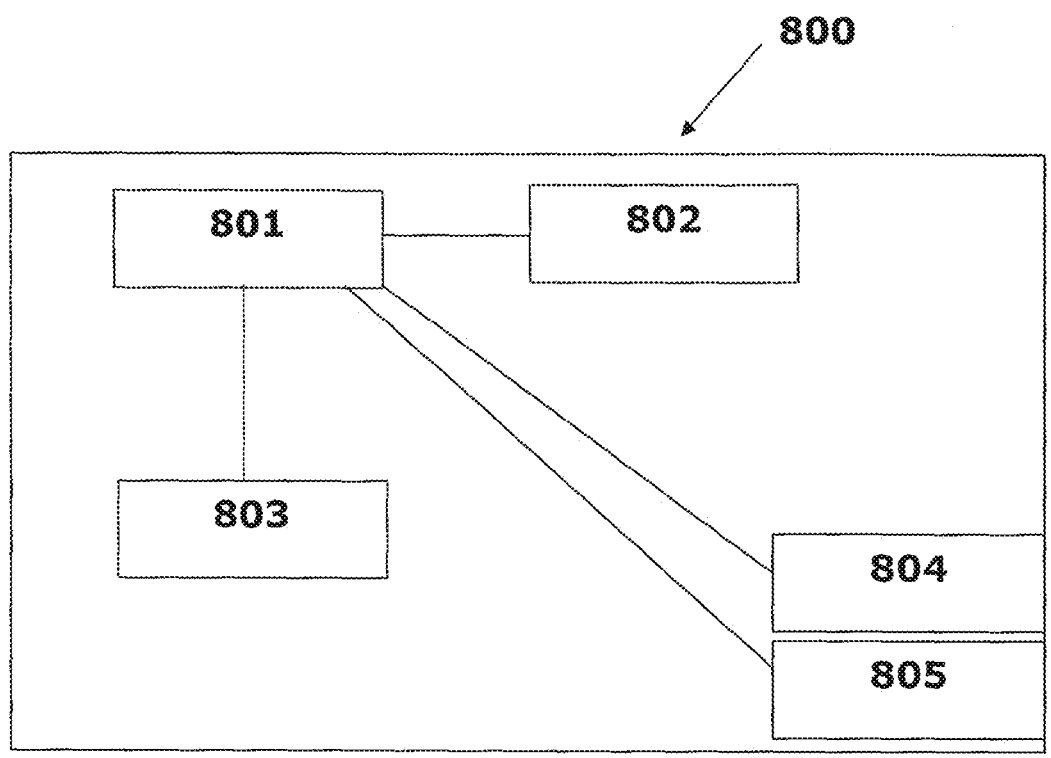
FIG. 8 illustrates schematically a detection device according to the present invention.

The data analysis unit 35, 800 may comprise any suitable type of processing device 801 (as illustrated in FIG. 8) such as a microprocessor, ASIC (Application Specific Integrated Circuit), FPGA (Field Programmable Gate Array), or similar. It may further comprise at least one memory 802 of volatile and/or non-volatile type (e.g. RAM, DRAM, hard disk, Flash memory, and so on) and a user interface unit 803. It may further comprise one or several communication or interconnectivity interfaces 804, e.g. network connection(s), keyboard, mouse, serial (e.g. RS232) and/or parallel connectors (Centronics), sensor signal input(s), ND and/or D/A converters (Analog/Digital), GPIB (General Purpose Interface Bus), VXI (VME eXtensions for Instrumentation), SCSI (Small Computer System Interface), Firewire, USB (Universal Serial Bus), and so on. However, these are generally known to the skilled person and not elaborated around further. The device may further comprise a separate interface 805 to the microwave transceiver 34; however, it should be noted that a transceiver interface may be in some applications through the interconnectivity interface 804.

Figure 4:
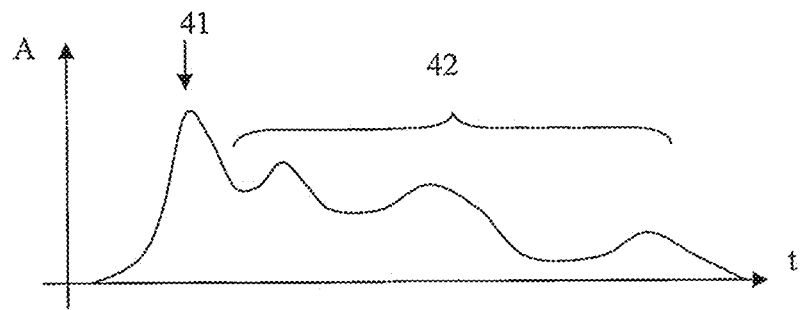
FIG. 4 illustrates schematically measured data converted into time-domain by means of an inverse Fourier transformation.
Figure 5:
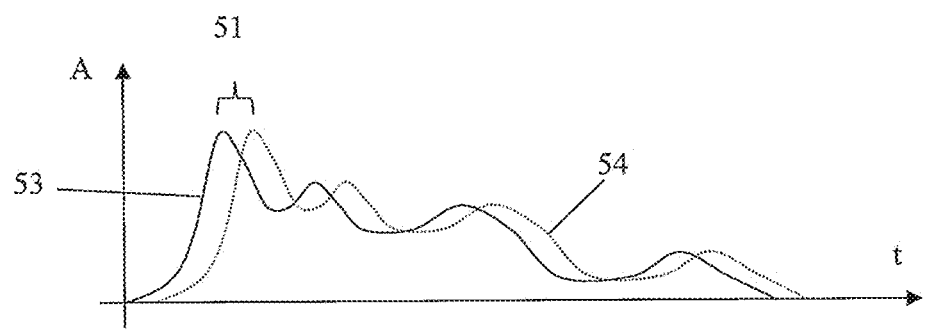
FIG. 5 shows how the inverse Fourier transformed data will change due to a movement of the body part being monitored. The dotted line corresponds to the original data and the solid line corresponds to the data acquired after a movement towards the antenna.

One problem in the analysis of the data is to differentiate between changes in the scattering data due to patient movement and a change due to the development of brain swelling or stroke. The current invention uses a method to compensate for patient movements and extracts the data of interest scattered from inside the skull. For that compensation method it is necessary to make a large number of measurements at different frequencies. The number of measurements could be from at least two up to 1000 or more in a bandwidth within the range 100 MHz-5 GHz or more. When the measurements have been made in the frequency domain an inverse Fourier transformation is performed to convert the data into a time domain signal. The signal will in principle look similar to what is shown in FIG. 4. The first peak 41 in the reflection data will most likely correspond to the reflection from the outer shell of the body, e.g. the skin; whereas, the rest of the signal 42 indicate reflections from internal tissues in the body. With a fixed antenna array a movement of the body part towards the antenna array during the monitoring will correspond to a movement of the first reflected peak 51 as shown in FIG. 5. The solid line 53 is a reference curve (theoretical or measured) which is to be compared to the dotted curve 54 indicating the current status from a new measurement.

Figure 6:
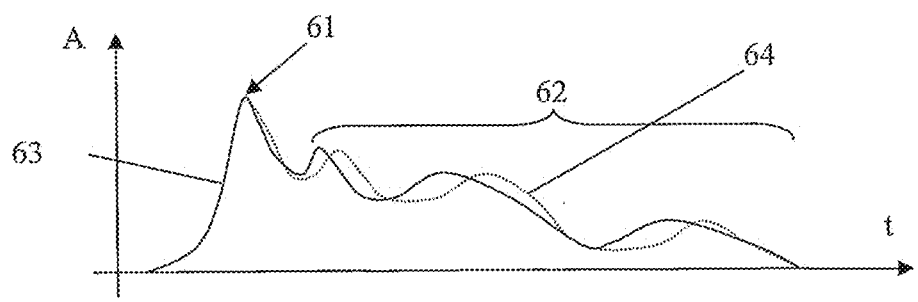
FIG. 6 shows that the important changes in the signal for the diagnosis are found in times after the first reflection from the skin. The dashed line shows the original appearance of the reflected signal measuring tissue in healthy conditions. The solid line shows a change in the signal corresponding to a change in the tissue of the inter-cranial tissue.

The internal changes of the brain tissue inside the skull will on the other hand lead to changes in the scattered radiation later in time with respect to the first reflection. In FIG. 6 a sketch of the principal behaviour of the signal is shown due to an increased volume of the brain. The first peak 61 represents the reflection at the outer shell and the rest of the signal indicates reflections from internal tissues. The solid line 63 is a reference representation (theoretical or measured) and the dotted line 64 is a measurement of the current situation. The difference between these two indicates that changes have occurred in the internal parts of the body. This may be used to determine that a change has occurred and in some applications what type of change and the extent of this change. As measurements are continuously made and analyzed, changes that develop over time can be found and separated from movements of the patient. In that way a continuous monitoring of the changes inside the brain can be made. That is, it may be used at a hospital or some other caring facility for monitoring the development of an ailment under scrutiny; this may be done with a few seconds, minutes or hours interval or even faster or slower depending on the ailments progress over time. It may also be used for monitoring at home, in an ambulance, or in the field (e.g. at a place of an accident or a catastrophe scene).

In principle no new information is added to improve the analysis of the data through the inverse Fourier transformation described in FIGS. 4-6. All information necessary for the data analysis is already present in the frequency domain data originating directly from the measurements. As a part of this invention, the data analysis may therefore be performed directly on the frequency domain data using different algorithms.

Figure 7:
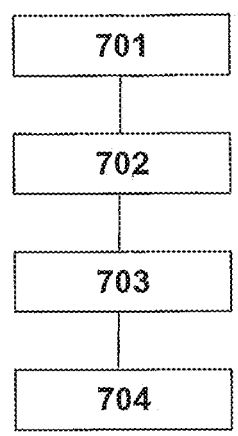
FIG. 7 illustrates schematically a method according to the present invention.

FIG. 7 illustrates a method according to the present invention, where in a first step 701 at least two measurements are sampled, these are statistically analyzed 702, inverse Fourier transformed into the time domain 703, and compared with reference data 704 in order to determine the current status as compared to reference data (such as from theoretical reference data or a previous measurement of the same body part or a reference body part).

The present invention may be realized as a system for the purpose of monitoring intra cranial properties of the brain based on microwave measurements. The proposed system uses one or more sources of microwave radiation to illuminate the skull and the same antenna system is used to receive the transmitted signals. The system may analyze the data in real time. Changes in the data over time may be used to monitor brain changes.

Indications of brain swelling and other changes may be based on continuous measurements and deviations from an initial state of the properties of the brain.

Circularly polarized radiation may be transmitted and the receivers are capable of receiving elliptically polarized radiation.

The system may use the orientation of the received polarization and the amplitude and phase information of the received fields in the data analysis.

The present invention may also be realized as a method to detect patient movements and compensate for that in order not to corrupt the data with movement artefacts.

In the present invention also a compensation scheme that is based on an inverse Fourier transform of the measured data into time domain. The analysis is based on the first reflection that comes from the skin. If the head is moved the first reflection will move correspondingly and thus the movement of the head can be monitored through the movement of the first reflection.

Furthermore, a monitoring algorithm is provided that is based on the time domain data following after the first reflection from the skin. This measured scattering data comes from inside the skull and are used by the monitoring algorithm to detect the swelling.

The monitoring algorithm where the measured data may be expressed as in equation (1) and changes in this representation is related to different injuries or diseases.

The monitoring algorithm may use the movement detection scheme for the purpose of excluding the data measured when the patient is moving from the analysis.

The system may also be used to detect abnormalities in other parts of the body than in the skull. This application includes, but is not limited to, detecting internal bleeding in the abdomen.

The system may be used to diagnose between ischemic and hemorrhagic stroke.

Hip Joint Monitoring

The scattered radiation is carrying the information utilized by this invention for the purpose of detecting and analyzing a possible dislocation of surgically implanted hip-joint prosthesis. The analysis could be based on the electromagnetic radiation scattered from the prosthesis between different occasions of examination and comparison with a measurement when the prosthesis is known to be in place. The measurement for comparison could for instance be made immediately after the surgery. When making examinations after this, microwave measurements of the scattering are compared to the measurement made with the prosthesis in place. Thus a deviation between the two measurements can be used as an indicator that something has happened to the prosthesis, on the other hand if the radiation patterns are the same it can be concluded that the prosthesis has not moved.

A specific procedure of the scattering measurement of the hip-prosthesis is also included in the invention and described here. The hip region is radiated with circularly polarized microwave radiation at a frequency that corresponds to the resonance frequency of the prosthesis. This should occur when the wavelength of the radiation is similar to or close to the length of the prosthesis. Depending on the orientation of the prosthesis elliptically reflected radiation could be measured at a number of positions outside the body. The orientation of the elliptical radiation bears information of the orientation of the prosthesis. In a similar way as described above comparison can now be made to a case measured when the prosthesis is known to be in place.

One problem associated with the comparison of data between the measurement with the prosthesis in its correct location and the measurement conducted at the time of examination where one wants to see if the prosthesis is still in its correct place is resolved by the following method. The problem is that it will not be possible to position the patient in exactly the same position with respect to the antennas as in the first measurement. Thus the radiation patterns between the two measurements might differ due to the different positioning of the patient between the examinations and thus it is not possible to isolate and the compare scattering from the prosthesis only. In this invention this problem is solved by implanting reradiating structures in the vicinity of the prosthesis with fixed and/or known positions that can be used as a reference system for the measurements. Alternatively it may also be possible to use some part of the human body as a constituent of the reference system if the scattered portion of the signal from that tissue can be isolated. The reference system could consist of implanted non-linear elements that have the effect of changing the frequency of the incoming radiation, RF-id tags might also be a possibility here. By an independent measurement of the new frequency generated by the non linear element it can be assumed that the measured scattering data is only generated by the reference system and therefore it is possible to compare data from different measurement occasions to determine the change in the positioning of the patient and to determine the viewing angle used for the measurements. Thus the scattering from the prosthesis may be related to the reference system when determining its location or possible dislocation. Once that is made the processing of the scattering data from the prosthesis can be made.

The measurement equipment in this case therefore needs to be capable of transmitting one frequency component and receiving another.

The current invention also contains a solution using the hip prosthesis as a radiating structure. The prosthesis is usually manufactured using materials such as titanium. Using a novel transceiver implant inside the prosthesis and a minor modification to the prosthesis the structure can be used as a radiating element. It is shown that this implanted radiating structure inside the human body will have a very distinct radiation pattern. Using this radiation pattern one can decide whether the structure has moved inside the human body. The patient can be scanned for the near field radiation pattern immediately after surgery. The radiation pattern is recorded and can be compared to later scans for finding abnormalities in a similar way as described above.

It should be noted that in this embodiment of the present invention, the device may be continuously worn at the hip joint and intermittently measure the condition of the joint and provide an alarm if the condition is outside a predetermined setting.

Furthermore, the solution according to the present invention provides a wearable portable monitoring device which may be used for home monitoring of body part to be monitored. This may be convenient for instance for monitoring stroke patients after treatment in hospital in a home or care environment.

It should be noted that the word "comprising" does not exclude the presence of other elements or steps than those listed and the words "a" or "an" preceding an element do not exclude the presence of a plurality of such elements. The invention can at least in part be implemented in either software or hardware. It should further be noted that any reference signs do not limit the scope of the claims, and that several "means", "devices", and "units" may be represented by the same item of hardware.

The above mentioned and described embodiments are only given as examples and should not be limiting to the present invention. Other solutions, uses, objectives, and functions within the scope of the invention as claimed in the below described patent claims should be apparent for the person skilled in the art.

The invention claimed is:

1. A device for obtaining a representation of the status of internal parts of a body part of a patient, comprising:
   a processing unit (35, 800);
   an interface (805) to a microwave transceiver (34);
   a display unit (36);
   wherein the processing unit is arranged to:
   repeatedly send a control signal to the microwave transceiver for generating a pulse of microwave radiation to be radiated from an antenna system comprised of at least one antenna (31) into the body part, the body part moving during said radiation of microwave radiation;
   receive signals, in frequency domain, indicative of received microwave radiation from the microwave transceiver;
   analyze the received signals with respect to time and amplitude, a first portion of the received signals being electromagnetic waves from radiation scattered directly off the skin of the patient and a second portion of the received signals being other electromagnetic waves from the other radiation penetrating into the patient and scattered off the internal tissues of the patient, the first portion of the received signals being a first-received reflection and the second portion of the received signals being a second-received reflection, the analysis including performing an inverse Fourier transform of received signals into time domain to time-separate and extract the first-received reflection from the second-received reflection;
   compensate for patient movements and extract data of interest indicating reflections from the internal tissues by assigning the extracted first-received reflection as an indication of patient body movement, and assigning the extracted second-received reflection as an indication of the internal tissues;
   compare the analyzed signals with theoretically or measured reference data; and
   determine the status of the internal part of the body from the comparison.

2. The device according to claim 1, wherein the device is arranged to analyze the received signals with reference to a brain.

3. The device according to claim 1, wherein the device is arranged to analyze the signals with reference to a hip joint.

4. The device according to claim 1, wherein the device is arranged to analyze the signals with reference to an initial measurement of the internal part of the body.

5. The device according to claim 1, wherein the processing unit is arranged to use information relating to polarization, amplitude, and phase in analysis.

6. A method for obtaining a representation of the status of internal parts of a body, comprising the steps of
   repeatedly sending a control signal from a processing unit to a microwave transceiver, the body moving during said radiation of microwave radiation;
   receiving signals, in frequency domain, indicative of microwave signals from the microwave transceiver;
   analyzing the received signals with respect to time and amplitude, a first portion of the received signals being electromagnetic waves from radiation scattered directly off the skin of the patient and a second portion of the received signals being other electromagnetic waves from the other radiation penetrating into the patient and scattered off the internal tissues of the patient, the first portion of the received signals being a first-received reflection and the second portion of the received signals being a second-received reflection, the analysis including performing an inverse Fourier transform of received signals into time domain to time-separate the first-received reflection form the second-received reflection;
   compensating for patient movements and extracting data of interest indicating reflections from the internal tissues by assigning the extracted first-received reflection as an indication of patient body movement, and assigning the extracted second-received reflection as an indication of the internal tissues;
   comparing the analyzed signals with theoretically or measured reference data; and
   determining the status of the internal parts of the body using the comparison in a continuous manner.

7. A system for obtaining a representation of the status of internal parts of a body, comprising:
   a processing unit (35, 800);
   a microwave generating unit (34);
   a microwave receiving unit (34);
   a microwave transmitting antenna (31);
   a microwave receiving antenna (32);
   wherein the processing unit is arranged to control the microwave generating unit to generate a pulse of microwave radiation transmitted using the microwave transmitting antenna arranged to obtain signals from the microwave receiving unit in turn using the microwave receiving antenna for receiving signals, in frequency domain, reflected from internal parts of the body while the body is moving, and arranged to analyze the obtained signals with respect to time and amplitude, a first portion of the received signals being electromagnetic waves from radiation scattered directly off the skin of the patient and a second portion of the received signals being other electromagnetic waves from the other radiation penetrating into the patient and scattered off the internal tissues of the patient, the first portion of the received signals being a first-received reflection and the second portion of the received signals being a second-received reflection, the analysis including performing an inverse Fourier transform of received signals into time domain to time-separate and extract the first-received reflection from the second-received reflection, compensate for patient movements and extract data of interest indicating reflections from the internal tissues by assigning the extracted first-received reflection as an indication of patient body movement, and assigning the extracted second-received reflection as an indication of the internal tissues compare a result of the analyzing the obtained signals with reference data, and obtain a representation of the internal parts of the body.

8. The system according to claim 7, wherein the transmitting antenna and the receiving antenna are separate, spaced-apart antennas.

9. The system according to claim 7, wherein the transmitting antenna and the receiving antenna are a combined antenna.

10. The system according to claim 7, wherein the transmitting antenna and the receiving antenna comprise a plurality of antennas arranged in a pattern at least partly surrounding the body part.

11. The system according to claim 7, wherein the transmitting antenna is arranged to transmit circularly polarized radiation and the receiving antenna is arranged to receive at least elliptically polarized radiation.

12. The system according to claim 7, wherein the processing unit is arranged to use information relating to polarization, amplitude, and phase in analysis.

13. The system according to claim 7, wherein the processing unit is arranged to continuously monitor the status of a brain.

14. The system according to claim 7, wherein the processing unit is arranged to detect volumetric or pressure changes relating to the brain.

15. The system according to claim 7, being arranged as a portable unit.

16. The system according to claim 7, being arranged as a wearable unit.

17. The system according to claim 7, where the processing unit is arranged to determine a position vector, wherein the position vector is a multi-dimensional vector, and wherein the position vector is expressed as:

$$X=(s_{11}(\omega_1), s_{12}(\omega_1), \ldots, s_{nn}(\omega_1), s_{11}(\omega_2), \ldots, s_{nn}(\omega_m))$$

for a system comprising n number of antennas and m number of frequencies, wherein s are matrix elements comprised in the position vector and where $\omega$ are frequencies.

* * * * *